(12) United States Patent
Tu et al.

(10) Patent No.: US 6,206,842 B1
(45) Date of Patent: Mar. 27, 2001

(54) ULTRASONIC OPERATION DEVICE

(76) Inventors: Lily Chen Tu; Hosheng Tu, both of 2151 Palermo, Tustin, CA (US) 92782

( * ) Notice: Subject to any disclaimer, the term of this patent is extended or adjusted under 35 U.S.C. 154(b) by 0 days.

(21) Appl. No.: 09/128,452

(22) Filed: Aug. 3, 1998

(51) Int. Cl.[7] ............................................. A61H 1/00
(52) U.S. Cl. ............... 601/2; 601/3; 601/46; 600/437; 600/439; 606/41; 606/169; 606/170; 606/171; 604/22; 607/2; 607/76
(58) Field of Search ................... 601/2, 46, 34, 601/3, 65, 67, 68, 69, 70, 72; 606/41, 42, 110, 112, 191, 197; 604/22, 23, 19, 27, 36, 514, 515, 517; 128/24; 607/2, 76, 115, 116, 138, 133, 149

(56) References Cited

U.S. PATENT DOCUMENTS

| | | | |
|---|---|---|---|
| 5,295,484 | * 3/1994 | Marcus et al. | 128/660.03 |
| 5,471,988 | * 12/1995 | Fujio et al. | 128/660.03 |
| 5,484,398 | * 1/1996 | Stoddard | 604/22 |
| 5,971,949 | * 10/1999 | Levin et al. | 604/22 |
| 5,989,208 | * 11/1999 | Nita | 604/22 |
| 6,007,530 | * 12/1999 | Dornhofer et al. | 606/1 |

* cited by examiner

Primary Examiner—Marvin M. Lateef
Assistant Examiner—Jeoyuh Lin

(57) ABSTRACT

A medical device for treating the hemorrhoid or airway obstructions by reducing the mass of cellular tissues, wherein an elongate tubular shaft includes at least one ultrasonic transducer means disposed at its distal section of the shaft and facing one side of the shaft, an ultrasonic energy generating means, and a means for generating vibration at the distal section of the tubular element to effect the ablation having an additional vibrational massage therapy for the tissues.

18 Claims, 6 Drawing Sheets

ULTRASONIC OPERATION DEVICE

The present invention generally relates to an improved ultrasonic ablation device and methods for treating hemorrhoids, polyps, vascular tissues, and natural conduit obstructions in a patient by delivering ultrasonic energy to the target tissue sites in association with therapeutic pressure management.

BACKGROUND OF THE INVENTION

One method of modifying cellular tissues in situ requires heating the tissues, and causing them to shrink and tighten. It is often less traumatic than surgical procedures and may be the only alternative method, wherein other procedures may be unsafe, complicate, or ineffective. Ablative treatment devices have an advantage because of using a destructive energy that is rapidly dissipated and reduced to a non-destructive level by conduction and convection, to forces of circulating fluids and other natural processes.

The destructive energy used includes microwave energy, radiofrequency energy, ultrasonic energy, cryogenic means, laser energy, and tissue destructive substances. They have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna, through a duct, to the area of treatment, and applying energy diffusely through the duct wall into the surrounding tissues in the targeted directions.

Of particular interest to the present invention are ultrasonic energy therapeutic protocols, which have been proven to be highly effective. The traditional radiofrequency ablation provides therapeutic energy by heat conduction while the ultrasonic ablation can provide a deeper energy penetration by remote energy transmissions. By heating the tissues deeply, and causing them to shrink and tighten, the loosen tissue can be tightened and restored to its healthy state. Ultrasonic energy, when coupled with a temperature control mechanism, can be supplied to the device-to-tissue contact site and deep into the tissue zone precisely to obtain the desired tissue treatment. Ultrasonic energy is conveyed to the tissue by heat conduction and remote penetration.

To be more efficient in ultrasonic energy ablation, an ultrasonic transducer means with a vibration capability can be used to simultaneously deliver the massage therapy to the target tissues. The electric toothbrush with vibration has been disclosed in the following patents: Suyama in U.S. Pat. No. 4,944,296, Ng in U.S. Pat. No. 5,283,921, Hwang in U.S. Pat. No. 5,381,576, Okada in U.S. Pat No. 5,421,726, Mei in U.S. Pat. No. 5,617,603, and Hahn in U.S. Pat. No. 5,651,157. All the above patents disclose the advantage of an electric toothbrush with vibration. However, they do not teach using an ablation means with vibration capability to treat the tissues for therapeutic purpose.

On the other hand, Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissues point, it is not disclosed that the particular needle electrode could possibly combine pressure therapy and ultrasonic energy for proper contact with the target tissues. The "pressure therapy" is defined in this invention as applying appropriate pressure onto the tissues by a medical device.

Hemorrhoid is a varicose dilatation of a vein of the superior or inferior hemorrhoidal plexus, resulting from a persistent increase in venous pressure. The external hemorrhoid is a varicose dilatation of a vein of the inferior hemorrhoidal plexus, situated distal to the pectinate line and covered with modified anal skin. The internal hemorrhoid is a varicose dilatation of a vein of the superior hemorrhoidal plexus, originating above the pectinate line, and covered by mucous membrane. A more serious case of hemorrhoid, prolapsed hemorrhoid, is an internal hemorrhoid that has descended below the pectinate line and protruded outside the anal sphincter. One of the worst cases, strangulated hemorrhoid, is an internal hemorrhoid which has been prolapsed sufficiently and for long enough time for its blood supply to become occluded by the constricting action of the anal sphincters.

Taylor in U.S. Pat. No. 5,578,047 teaches a hemorrhoid-removing device. Tuffel in U.S. Pat. No. 4,938,221 teaches a hemorrhoid inflammation-reducing device. Bidoia in U.S. Pat. No. 5,203,863 teaches an instrument for the ligation of hemorrhoids. None of them discloses a medical device by using a suitable energy to treat a dilated vein to shrink it. On the other hand, an alternative for hemorrhoid treatment is by surgically removing the dilated vein by a laser or other means. For a dilated vein, RF energy or other suitable energy can be applied for treating the tissues of the vascular walls, and causing them to shrink and tighten.

Marcus et al. in U.S. Pat. No. 5,295,484 and Castellano et al. in U.S. Pat. No. 5,606,974 teach a catheter system having ultrasonic device for intracardiac ablation of arrhythmias. However, neither discloses a medical device having ultrasonic energy and pressure/vibrational therapy to treat the hemorrhoid tissues effectively.

Therefore, there is a need for an improved medical device and methods using the ultrasonic energy to treat a dilated vein or tissue, such as hemorrhoids or tumors, while simultaneously applying pressure and/or vibrational massage therapy.

SUMMARY OF THE INVENTION

In general, it is an object of the present invention to provide a method and an improved medical device for generating heat, to treat the hemorrhoids, dilated vascular vessels, or other cellular tissues. It is another object of the present invention to provide a medical device so that vibrational massage therapy can be applied to the hemorrhoids, or the target cellular tissues, for intimate contact. It is another object of the present invention to provide a device utilizing ultrasonic transducer means for tissue treatment. It is still another object of the present invention to provide a method and a device for monitoring the temperature of the medical device, and to control the temperature by utilizing a temperature control mechanism and/or algorithm. The location of the temperature sensor means is preferably at close proximity of the ultrasonic transducer means of the medical device. It is still another object of this invention to provide a method and a device for treating hemorrhoids, dilated vascular vessels, or cellular tissues in a patient by applying appropriate pressure to the tissues.

In summary, heat is generated by supplying a suitable energy source to a device, that is comprised of an energy delivery or electrode means, in contact with the body tissues. A suitable energy source may consist of radiofrequency energy, microwave energy, ultrasonic energy, alternating current energy, or laser energy. The energy can be applied to the hemorrhoids or cellular tissues through the energy delivery or electrode means. A DIP (dispersive indifferent pad) type pad or electrode, which contacts the patient, is connected to the Indifferent Electrode Connector port on the ultrasonic energy generator. The generator should usually be grounded to avoid electrical interference. Heat is controlled by the power of the ultrasonic energy delivered and by the delivery duration. The standard ultrasonic energy generator means, and its applications through the ultrasonic transducer means, to a patient are well known for those who are skilled in the art. More detailed information can be found in U.S. Pat. No. 5,295,484.

The present invention comprises at least one ultrasonic transducer mounted on a distal end portion of a device. The ultrasonic transducer may be a single crystal transducer or a phased array crystal transducer. Ultrasonic transducers adapted for use in the invention are those capable of generating frequencies in the 1–40 MHz range under an applied electrical energy of 1 watt or above. Ultrasonic transducers are typically composed of relatively brittle piezoelectric crystalline material that is somewhat fragile. The ultrasonic transducers may be manufactured in different shape and size. In one embodiment, for energy deep penetration purposes, the ultrasonic transducer has a sharp needle-like end or studded nails to effect the "pressure therapy". The ultrasound transducer further comprises ultrasound crystals adapted to generate at least one of focused ultrasound energy or diffused ultrasound energy.

In an optional embodiment, means for generating vibration at the distal section comprises a motor mounted in the cavity of the handle, which has a rotatable motor shaft, an elongated connecting shaft having a first end, to which the distal end portion having at least an ultrasonic transducer is connected, and a second end connected to the handle, a weight eccentrically mounted on the motor shaft with respect to the motor shaft axis, so as to rotate eccentrically, so that when the motor shaft rotates, the distal end portion of the device vibrates.

In one optional embodiment, the device is leak-proof so that the therapeutic agent, in either fluid phase or gel phase, can be diffused under a positive pressure to flow inside the lumen of the medical device from its proximal end to the distal end. The fluid is vented through an optional opening at close proximity of the electrode to effect the therapeutic purpose.

The method and medical device of the present invention has several significant advantages over other known systems or techniques to treat the hemorrhoids, dilated vascular vessels, tumors, or polyps. In particular, the device system comprising the electrode means, using ultrasonic energy as a heat source, in this invention and simultaneously applying pressure therapy to the tissues, is highly desirable in its intended application on the hemorrhoid or on other medical ablation applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
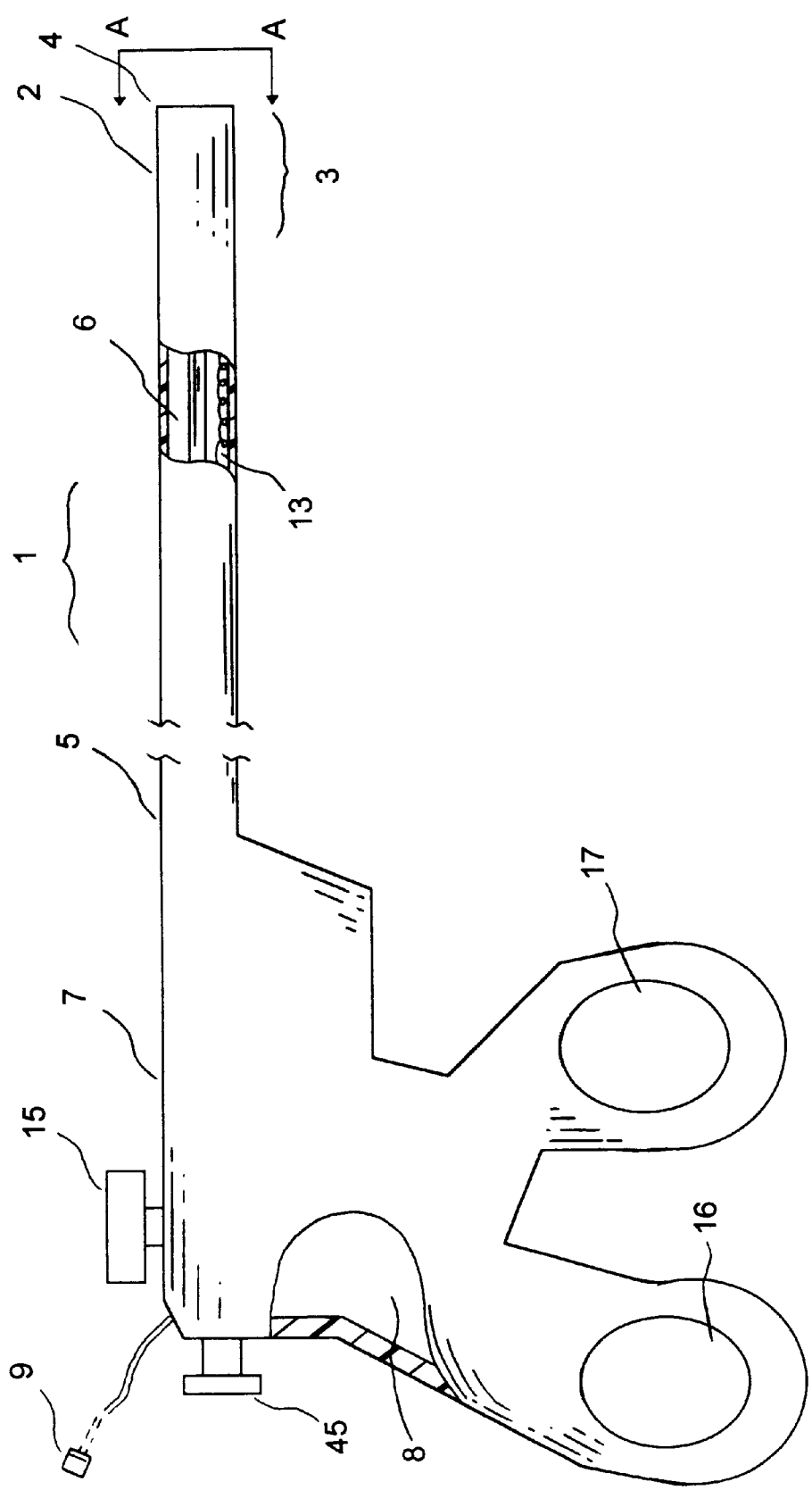
FIG. 1 is an overall view of the medical device, comprising at least one ultrasonic transducer, constructed in accordance with the principles of the present invention.
Figure 2:
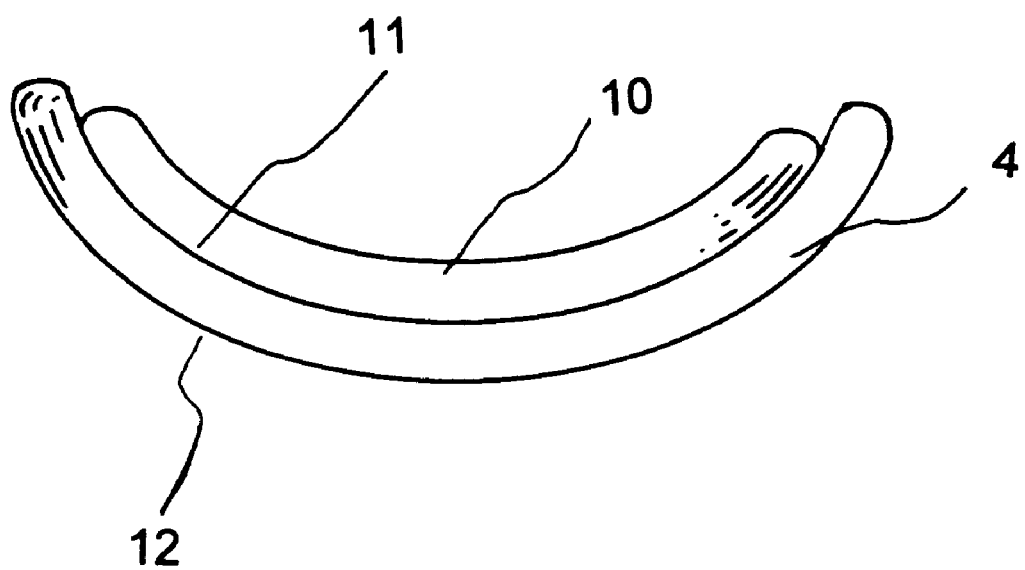
FIG. 2 is a front view of the distal end of the medical device, section A—A, in FIG. 1.

Referring to FIGS. 1 to 6, what is shown is an embodiment of the medical device system, comprising simultaneously applying ultrasonic energy and applying a pressure therapy to treat the hemorrhoids, airway obstructions, polyps, or other cellular tissues of a patient. As shown in FIG. 1, the medical device 1 in the form of an elongate tubular assembly comprises an elongate tubular shaft 2 having a distal section 3, a distal end 4, a proximal end 5, and at least one lumen 6 extending therebetween. The distal section has a first side and a second opposite side. A handle 7 is attached to the proximal end 5 of the elongate tubular shaft 2, wherein the handle has a cavity 8. A connector means 9 is attached to the handle 7. Referring to FIG. 2, at least one ultrasonic transducer 10 is mounted on the distal section 3 of the elongate tubular shaft 2, wherein the ultrasonic transducer 10 is mounted on the first side 11 of the elongate tubular shaft 2. In other words, the second opposite side 12 of the elongate tubular shaft 2 has no ultrasonic transducer and is insulative to the ultrasonic energy delivery. Ultrasonic energy from one of the at least one ultrasonic transducer to emit from the first side outwardly, the ultrasonic transducer being in an essentially transverse semi-circular concave shape, wherein the ultrasonic transducer is adapted to be placed in contract with biological tissues and adapted to provide therapeutic energy of ultrasonic microvibration. The elongate tubular shaft may be made of a semi-flexible non-conductive material. In one embodiment, the elongate tubular shaft is made of a thermoplastic elastomers, such as polyurethane, silicone, fluoroelastomers, and the like.

An electrical conductor 13 passes through a lumen 6 of the tubular shaft 2; wherein the electrical conductor is connected to the at least one ultrasonic transducer 10. The medical device system 1 also comprises an ultrasonic energy generating means (not shown here), wherein the ultrasonic energy is supplied to the at least one ultrasonic transducer 10 through the electrical conductor 13.

One on-off control knob 15 is used to control the ultrasonic energy delivery to the ultrasonic transducer 10. The handle 7 has a thumb holder 16 and a finger holder 17 to guide the device to the appropriate location of the targeted tissue site.

FIG. 2 shows a front view of the distal end 4 of the medical device, section A—A, in FIG. 1. The distal section 3 comprises an essentially transverse semi-circular concave elongate shaft, wherein the concave curve is essentially perpendicular to a reference axis, wherein the ultrasonic transducer 10 in a semi-circular concave shape sits securely on the inner side 11 of the semi-circular distal section 3 and adapted to contact the tubular biological tissue, such as a hemorrhoid or a vascular vessel wall, from the concave side or the first side 11.

Figure 3:
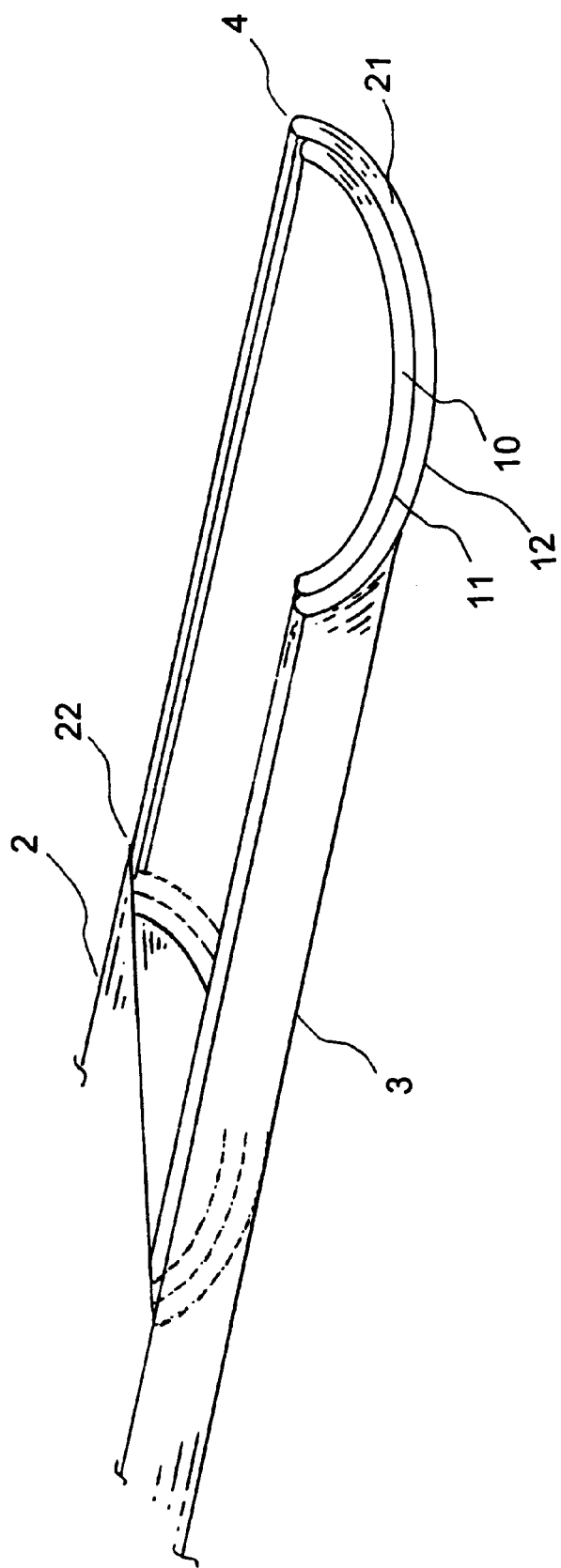
FIG. 3 is a perspective view of the distal section comprising at least one ultrasonic transducer.

FIG. 3 shows a side cross-sectional view of the distal section 3 of the medical device. An ultrasonic transducer means 10 is disposed at the distal portion of the distal section 3 of the tubular shaft 2. The ultrasonic transducer is mounted on the first side 11 of the tubular shaft. A conductor 13 is connected to the ultrasonic transducer 10 for transmitting the ultrasonic energy. The end-shaft 21 at the distal portion of the elongate tubular shaft 2 where an ultrasonic transducer 10 is located, has an inner side 11 and an outer side 12. The end-shaft 21 extends to the line 22 to form an effective length for ultrasonic therapy between locations 4 and 22. In one embodiment, the ultrasonic transducer 10 is equipped with a studded surface, that points its studded surface to the inner side 11 facing the target tissue.

Figure 4:
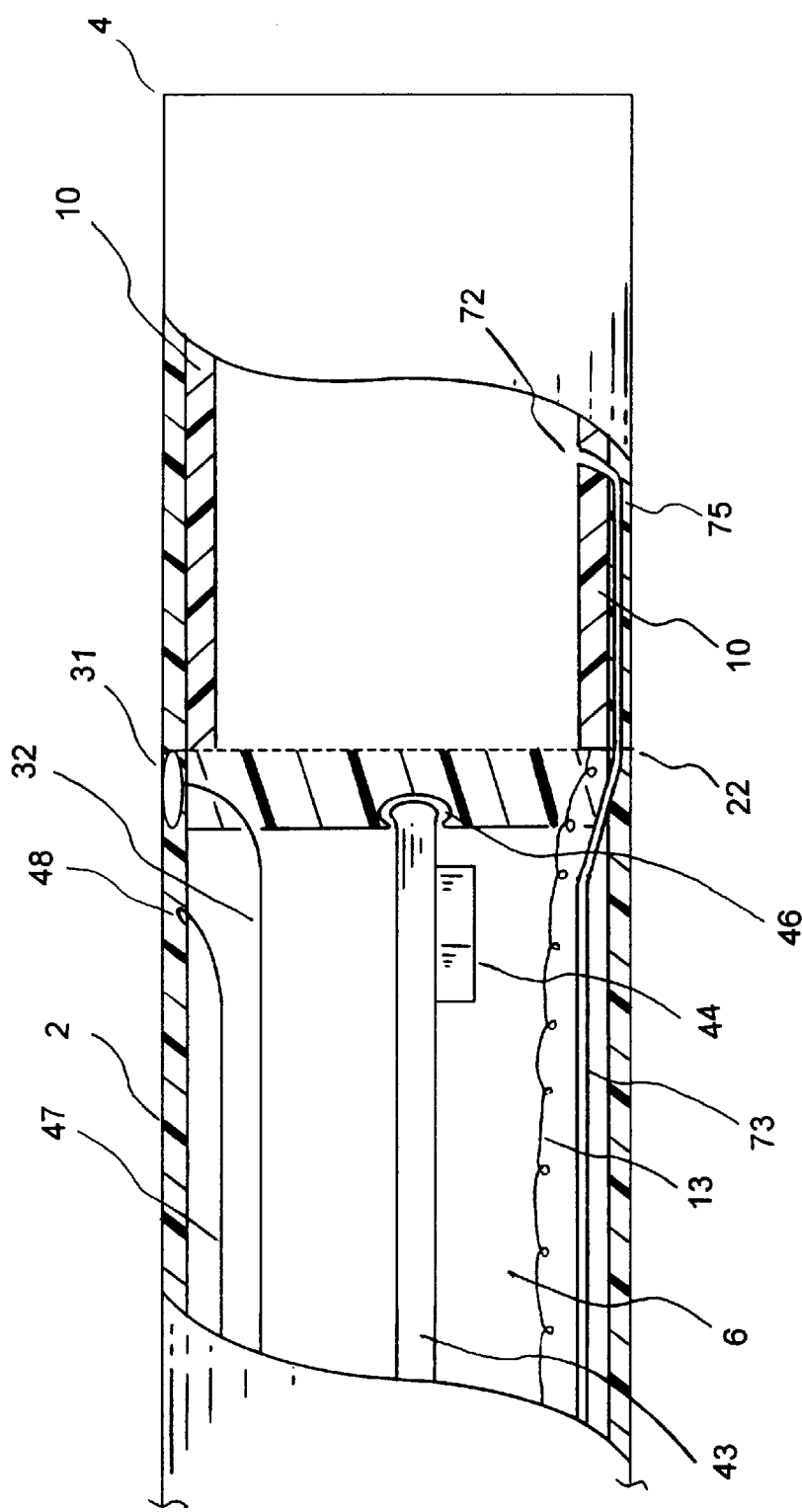
FIG. 4 is a side cross-sectional view of the distal section of the medical device in FIG. 1.

FIG. 4 shows a side cross-sectional view of the distal section of the medical device in FIG. 1. In one embodiment, at least one temperature sensing means 31 is disposed on the distal section of the elongate tubular shaft-close to the ultrasonic transducer 10. Insulated temperature sensing wire means 32 passes from the temperature sensing means 31 at the distal end portion, to an external temperature control mechanism through an outlet connector 9. The ultrasonic energy delivery is controlled by using the measured temperature from the temperature sensing means 31, through a closed-loop temperature control mechanism and/or algorithm. When the measured temperature rises to the preset high-limit point, the temperature control mechanism sends out a signal to cut off the ultrasonic energy supply. In a similar manner, when the measured temperature drops to the preset low-limit point, the temperature control mechanism sends out a signal to activate the ultrasonic energy supply.

Figure 5:
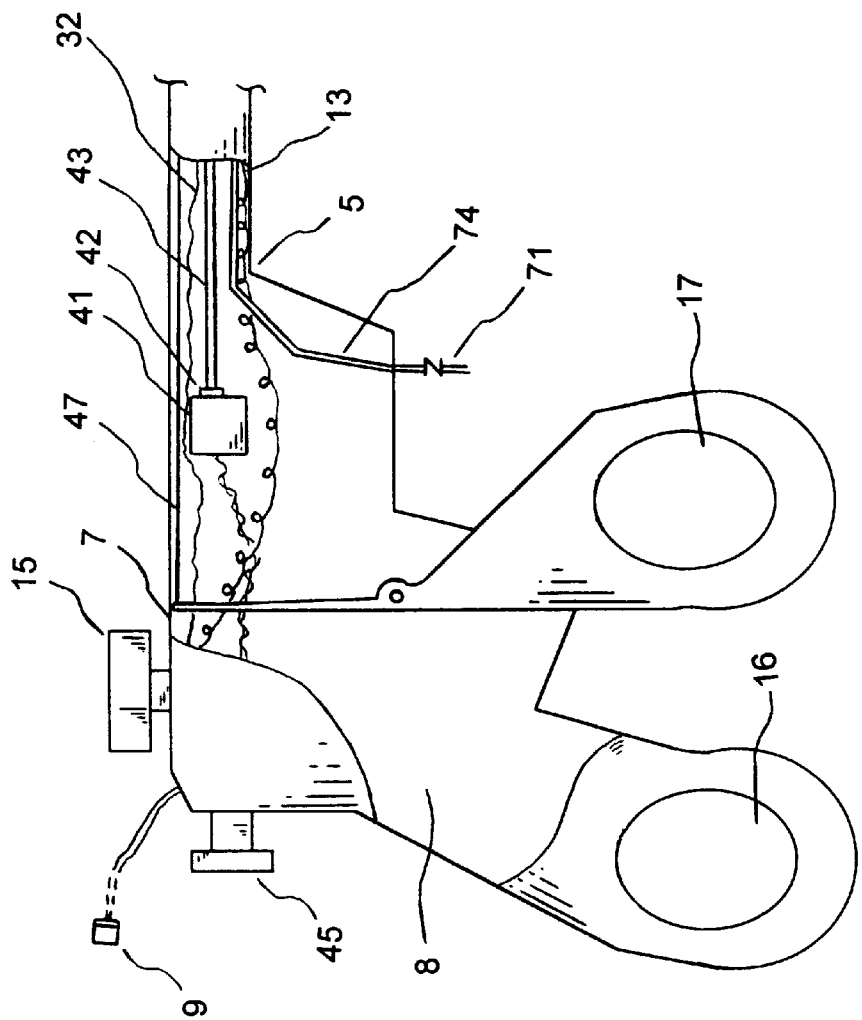
FIG. 5 is a cross-sectional view of the handle portion of the medical device.

In addition to the above-described medical device, FIG. 5 shows a cavity 8 inside the handle 7, in which a motor 41 is located. The medical device system further comprises means for generating vibration at the distal end portion of the medical device system, wherein the means for generating vibration at the distal end portion comprises a motor 41 mounted in the cavity 8 of the handle 7. The vibrating means comprises a rotatable motor shaft 42, an elongate connecting shaft 43 having a first end to which the distal section is connected, and a second end connected to the handle 7, a weight 44 eccentrically mounted on the motor shaft 43 with respect to the motor shaft axis, so as to rotate eccentrically. When the motor shaft 43 rotates, the distal section 3 of the medical device system generates vibration at a frequency range.

In one embodiment, a battery means (not shown), which is located at the proximal end of the cavity 8 of the handle 7, is used to supply the energy to the motor 41. In an alternate embodiment, the motor 41 is powered by an alternate current (AC) through a power input plug (not shown). In either case, the power supply is controlled by an on-off switch button 45 located conveniently on the handle 7. This alternate device has also the electrical conductors and temperature sensing wires as described in the above-described embodiment.

The vibrational shaft 43 with a ball-type bulge end is loosely and securely held in a hollow pocket at a point 46. The hollow pocket is part of the end-line 22 of the ultrasonic transducer means 10. Attached to the shaft 43 there is an eccentric weight 44. The eccentric rotation of the weight 44 places the distal section 3 into vibration via the shaft 43 due to the unbalancing effect of the eccentric weight 44. The vibrational amplitude is determined by the geometry of the shaft 43, the mass and configuration of the weight 44, and the rotational speed of the motor 41, among other factors.

In another embodiment as shown in FIG. 5, a fluid infusion means 71 is provided for the irrigation of a desired therapeutic agent, in either fluid phase or gel phase, to the hemorrhoids or to the target cellular tissue site. The fluid is adapted to diffuse out of the elongate tubular shaft 2 at an opening 72 in close proximity of or through the ultrasonic transducer 10. The therapeutic agent is selected from the group consisting of heparin solution, saline solution, fluoroquinolone, lactic acid, glycolic acid, alpha hydroxy organic acids, vitamins solution, povidone-iodine, nitrate compounds, virucidal agents, anti-inflammatory agents, antibiotics and/or their mixtures. A passage 73 is provided inside the lumen of the elongate tubular shaft 2 for transporting the fluid or gel from the passage proximal end 74 of the shaft 2 to the passage distal end 75. Thereafter the fluid or gel is diffused out of the device through the opening 72 over the exterior surface to provide a fluid protective layer surrounding the ultrasonic transducer wherein the ultrasonic transducer is adapted to be placed in contact with biological tissues.

FIG. 5 shows a cross-sectional view of the handle portion of the medical device. The distal section of the device system of this invention can be either a fixed curve type or a deflectable curve type. In an exemplary embodiment, the means for deflecting the distal section 3 comprises at least one steering wire 47 along with a support wire or an anchoring point 48 at the distal section 3. The steering wire 47 is usually attached to a radially offset location at its distal section. The means for selectively applying tension comprises a steering mechanism at the handle. In one embodiment, the steering mechanism is associated with and activated by the finger holder 17 which is connected to the steering wire 47.

Figure 6:
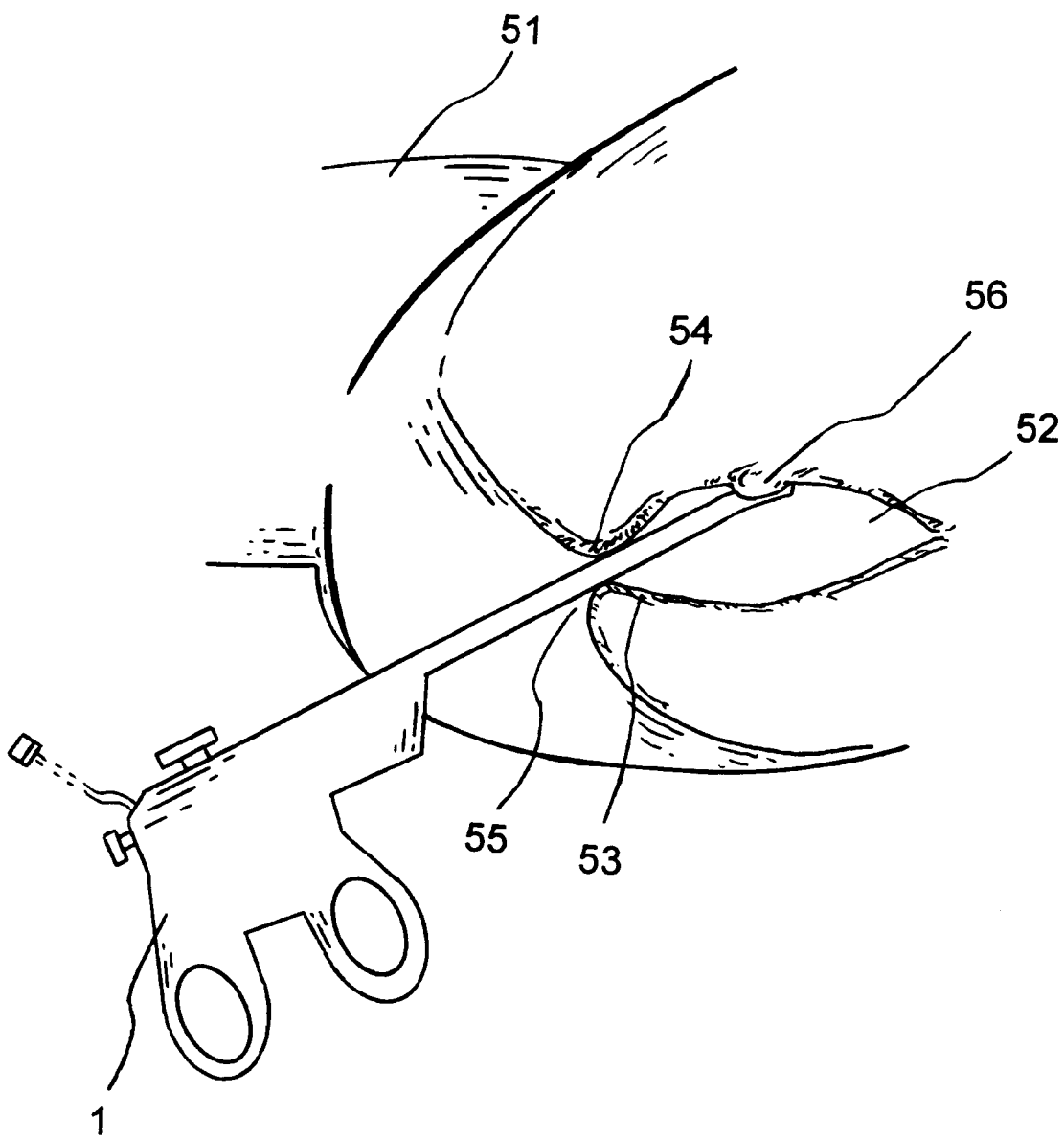
FIG. 6 shows a perspective view of a hemorrhoid region being treated by the medical device of the present invention.

FIG. 6 shows a perspective view of a hemorrhoid region being treated by the medical device of the present invention. For illustrative purposes, a brief anatomy of a patient in a supine position is shown in FIG. 6, wherein the thigh 51 and the groin section of the body is included. The lower part of the rectum 52 is confined by sphincter ani internus and sphincter ani externus 53. A pectinate line 54 separates the rectum 52 from an exterior portion of the body, wherein the opening for the rectum is the anal canal 55. An internal hemorrhoid 56 is also shown to illustrate their relative anatomical location for ablation purposes. The hemorrhoid 56 appears as a bump grown out of the tissue wall of the rectum 52. The hemorrhoidal bump 56 rises above the baseline and forms a mound by an excessive internal venous pressure. The vessel wall becomes dilated over a period of time, if not treated in time. The ultrasonic transducer 10 is in a concave fashion encircling the dilated vessel wall of the hemorrhoid bump 56. When simultaneously applying the pressure from the handle 7 and ultrasonic energy to the dilated vessel wall, the wall tissue contracts and tightens.

During procedures, the medical device is inserted into the rectum through an anal canal 55. A method of treating a hemorrhoid of a patient, the method comprises: (a) inserting a medical device through the anal canal for contacting the hemorrhoid of a patient, wherein the medical device comprises an elongate tubular shaft having a distal section, a distal end, a proximal end, and at least one lumen extending therebetween; a handle attached to the proximal end of the elongate tubular shaft, wherein the handle has a cavity; a connector means attached to the handle; at least one ultrasonic transducer mounted on the distal section of the elongate tubular shaft, wherein the ultrasonic transducer faces the first side of the elongate tubular shaft; an electrical conductor passing through a lumen of the tubular shaft; ultrasonic energy from one of the at least one ultrasonic transducer being adapted to emit from the first side outwardly, the ultrasonic transducer being in an essentially transverse semi-circular concave shape, wherein the ultrasonic transducer is adapted to be placed in contact with biological tissues and adapted to provide therapeutic energy of ultrasonic microvibration wherein the electrical conductor is connected to the at least one ultrasonic transducer; and an ultrasonic energy generating means, wherein the ultrasonic energy is supplied to the at least one ultrasonic transducer through the electrical conductor; (b) contacting the at least one ultrasonic transducer of the medical device against the cellular tissues of the hemorrhoid of a patient; (c) activating the ultrasonic transducer to direct ultrasonic energy at the hemorrhoid tissue region to be treated, thereby generating thermal energy in the tissue; and (d) heating the hemorrhoid tissue to a temperature and depth sufficient to ablate the hemorrhoid tissue, thereby reducing the size and mass of cellular tissues of the hemorrhoid.

As an alternative illustration, A method of treating a hemorrhoid of a patient, the method comprising the steps of: (a) inserting a medical device into the opening of a patient, wherein the medical device comprises at least one ultrasonic transducer mounted on the distal section thereof; (b) positioning the medical device to place the at least one ultrasonic transducer in close proximity to a tissue region to be treated; (c) activating the ultrasonic transducer to direct ultrasonic energy at the tissue region to be treated, thereby generating thermal energy and microvibration in the tissue; and (d) heating the target tissue to a temperature and depth sufficient to ablate the tissue, thereby reducing the size and mass of cellular tissues.

The external ultrasonic energy generator means has the capability to supply ultrasonic energy by controlling the time, power, and temperature through an optionally separate closed-loop temperature control means. The patient is connected to the ultrasonic energy generator means through a DIP electrode to form a closed-loop current system. Therefore, ultrasonic energy is applied and delivered to the targeted hemorrhoids region, through the ultrasonic transducers of this invention. The ultrasonic energy current in this invention is preferably within the range of 1 to 40 MHz. The electricity comprises applying at least 1 watt to the ultrasonic transducer. One material used to make piezoelectric transducers is barium titanate. The barium titanate has high sensitivity as an ultrasonic transducer, which means that it requires a small voltage amplification. Barium titanate is also substantially more durable under mechanical and environmental abuse than other piezoelectric crystals and can sustain its property at a relatively high temperature.

The frequency of the vibration of the medical device in this invention is preferably within the range of 60 to 1000 cycles per minute. By simultaneously applying ultrasonic energy to the ultrasonic transducers and by applying the pressure therapy, the hemorrhoid can be treated.

From the foregoing description, it should now be appreciated that a device system for the hemorrhoid and the treatment of vascular tissues, comprising a suitable energy source and a pressure therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A medical device system comprising:
    an elongate tubular shaft having a distal section, a distal end, a proximal end, and at least one lumen extending therebetween, wherein the distal section has a first side and a second opposite side;
    a handle attached to the proximal end of the elongate tubular shaft, wherein the handle has a cavity;
    a connector means attached to the handle;
    at least one ultrasonic transducer mounted on the distal section of the elongate tubular shaft, wherein one of said at least one ultrasonic transducer is mounted on said first side of the elongate tubular shaft, wherein ultrasonic energy from said one of said at least one ultrasonic transducer is adapted to emit from said first side outwardly, said ultrasonic transducer being in an essentially transverse semi-circular concave shape, wherein said ultrasonic transducer is adapted to be placed in contact with biological tissues and adapted to provide therapeutic energy of ultrasonic microvibration;
    an electrical conductor passing through one of said at least one lumen of the tubular shaft; wherein the electrical conductor is connected to said ultrasonic transducer; and
    an ultrasonic energy generating means, wherein the ultrasonic energy is supplied to said ultrasonic transducer through the electrical conductor.

2. The medical device system as in claim 1 further comprising means for generating vibration at the distal section of said elongate tubular shaft, wherein the means for generating vibration at said distal section comprises a motor mounted in the cavity of the handle, which has a rotatable motor shaft, an elongate connecting shaft having a first end to which the distal section is connected, and a second end connected to the handle, a weight eccentrically mounted on the motor shaft with respect to the motor shaft axis, so as to rotate eccentrically, so that when the motor shaft rotates, the distal section of said elongate tubular shaft generates vibration at a frequency range.

3. The medical device system as in claim 1 further comprising at least one temperature sensor, wherein one of said at least one temperature sensor is disposed on the distal section of said elongate tubular shaft.

4. The medical device system as in claim 2 further comprising a temperature control means, wherein the temperature measured from said one of the at least one temperature sensor is relayed to the temperature control means, said temperature control means being adapted to effect the ultrasonic energy supply to the medical device system.

5. The medical device system of claim 1, wherein the ultrasonic energy is adapted to affect said ultrasonic transducer sufficiently to cause said ultrasonic transducer to resonate with frequency of about 1 to 40 MHz.

6. The medical device system of claim 1, further comprising a hollow passage allowing flow of fluid within one of said at least one lumen of the elongate tubular shaft, a fluid inlet port at the handle, wherein the hollow passage is to provide fluid communication and flow of fluid originating from the fluid inlet port through said hollow passage to a portion of exterior surface of said ultrasonic transducer, wherein said exterior surface is on said same first side of the distal section of said elongate tubular shaft and adapted for said ultrasonic transducer to emit ultrasonic energy outwardly, said hollow passage directing the fluid flow from inside the elongate tubular shaft over the exterior surface to provide a fluid protective layer surrounding the ultrasonic transducer, wherein said ultrasonic transducer is adapted to be placed in contact with biologic tissues.

7. The medical device system of claim 2, wherein the frequency range of the vibration is within the range of 60 to 1000 cycles per minute.

8. The medical device system of claim 1, wherein said ultrasonic transducer further comprises ultrasound crystal adapted to generate at least one of focused ultrasound energy or diffused ultrasound energy.

9. The medical device system of claim 1, further comprising a steering mechanism at the handle adapted to deflect the distal section of the elongate tubular shaft.

10. A tissue treatment method for reducing the size and mass of cellular tissues of a hemorrhoid comprising the steps of:
(a) inserting a medical device through the anal canal for contacting the hemorrhoid of a patient, wherein the medical device comprises an elongate tubular shaft having a distal section, a distal end, a proximal end, and at least one lumen extending therebetween, wherein the distal section has a first side and a second opposite side; a handle attached to the proximal end of the elongate tubular shaft, wherein the handle has a cavity; a connector means attached to the handle; at least one ultrasonic transducer mounted on the distal section of the elongate tubular shaft, wherein one of said at least one ultrasonic transducer is mounted on said first side of the elongate tubular shaft, wherein ultrasonic energy from said one of said at least one ultrasonic transducer is adapted to emit from said first side outwardly, said ultrasonic transducer being in an essentially transverse semi-circular concave shape, wherein said ultrasonic transducer is adapted to be placed in contact with biological tissues and adapted to provide therapeutic energy of ultrasonic microvibration; an electrical conductor passing through one of said at least one lumen of the tubular shaft; wherein the electrical conductor is connected to said ultrasonic transducer; and an ultrasonic energy generating means, wherein the ultrasonic energy is supplied to said ultrasonic transducer through the electrical conductor;
(b) contacting said ultrasonic transducer against the cellular tissues of the hemorrhoid of a patient;
(c) activating said ultrasonic transducer to direct ultrasonic energy at the hemorrhoid tissue region to be treated, thereby generating thermal energy in the tissue; and
(d) heating the hemorrhoid tissue to a temperature and depth sufficient to ablate the hemorrhoid tissue, thereby reducing the size and mass of cellular tissues of the hemorrhoid.

11. The treatment method as in claim 9, the step further comprising the step of generating vibration at the distal section of said elongate tubular shaft, wherein the step of generating vibration at the distal section comprises a motor mounted in the cavity of the handle, which has a rotatable motor shaft, an elongate connecting shaft having a first end to which the distal section of the elongate tubular shaft is connected, and a second end connected to the handle, a weight eccentrically mounted on the motor shaft with respect to the motor shaft axis, so as to rotate eccentrically, so that when the motor shaft rotates, the distal section of said elongate tubular shaft vibrates.

12. The treatment method as in claim 10, the step further comprising initiating vibration to the distal section of said elongate tubular shaft to effect the vibrational therapeutic massage for treating the tissues.

13. The treatment method as in claim 9, the step further comprising the device having at least one temperature sensor, wherein one of said at least one temperature sensor is disposed at close proximity of said ultrasonic transducer of the elongate tubular shaft.

14. A tissue treatment method for reducing the size and mass of cellular tissues comprising the steps of:
(a) inserting a medical device into the opening of a patient, wherein the medical device comprises at least one ultrasonic transducer mounted on the distal section thereof;
(b) positioning the medical device to place one of said at least one ultrasonic transducer to a tissue region to be treated, wherein said one of said at least one ultrasonic transducer is adapted to be placed in contact with cellular tissues;
(c) activating said ultrasonic transducer to direct ultrasonic energy at the tissue region to be treated, thereby generating thermal energy and microvibration in the cellular tissues; and
(d) heating the cellular tissues to a temperature and depth sufficient to ablate the cellular tissues, thereby reducing the size and mass of said cellular tissues.

15. The treatment method as in claim 13, the step further comprising the step of generating vibration at a distal section of the medical device, wherein the step of generating vibration at the distal section comprises a motor mounted in a cavity of a handle of the medical device, which has a rotatable motor shaft, an elongate connecting shaft having a first end to which the distal section of the medical device is connected, and a second end connected to the handle, a weight eccentrically mounted on the motor shaft with respect to a motor shaft axis, so as to rotate eccentrically, so that when the motor shaft rotates, the distal section of the medical device vibrates.

16. The treatment method of claim 14, the step further comprising initiating vibration to the distal section of the medical device to effect the vibrational therapeutic massage for treating cellular tissues.

17. The treatment method of claim 13, wherein the step of activating said ultrasonic transducer further comprises the step of applying electrical energy to said ultrasonic transducer sufficiently to cause said ultrasonic transducer to resonate with frequency of about 1 to 40 MHz.

18. The treatment method of claim 13, wherein said medical device further comprises a hollow passage within a lumen of said medical device, a fluid inlet port, wherein the hollow passage is to provide fluid communication and flow of fluid originating from the fluid inlet port through said hollow passage to a portion of an exterior surface of said ultrasonic transducer, wherein said exterior surface is adapted for said ultrasonic transducer to emit ultrasonic energy outwardly, said hollow passage directing the fluid flow from inside said medical device over the exterior surface to provide a fluid protective layer surrounding the ultrasonic transducer, wherein said ultrasonic transducer is adapted to be placed in contact with cellular tissues.

* * * * *